United States Patent [19]

Dwivedi et al.

[11] 4,376,198

[45] Mar. 8, 1983

[54] PROCESS FOR THE MANUFACTURE OF GLUCOSYLSORBITOL

[75] Inventors: Basant K. Dwivedi; Subodh K. Raniwala, both of Randolph, N.J.

[73] Assignee: Chimicasa GmbH, Switzerland

[21] Appl. No.: 305,694

[22] Filed: Sep. 25, 1981

Related U.S. Application Data

[63] Continuation of Ser. No. 111,272, Jan. 11, 1980, abandoned.

[51] Int. Cl.³ .................... C07H 15/02; C07H 15/04
[52] U.S. Cl. ..................................... 536/4.1; 426/548
[58] Field of Search ....................... 536/4, 1; 426/548

[56] References Cited

U.S. PATENT DOCUMENTS 3,766,165 10/1973 Rennhart ............................... 536/1
4,024,290 5/1977 Layton ................................. 426/548

*Primary Examiner*—Blondel Hazel
*Attorney, Agent, or Firm*—Richard P. Crowley

[57] ABSTRACT

A process of preparing glucosylsorbitol suitable for direct use as a food-bulking agent, which process consists essentially of heating equimolar quantities of a mixture of glucose and sorbitol under vacuum in the presence of an effective amount of a nontoxic, edible di or tri carboxylic acid or acid anhydride as an acid catalyst, to provide a nontoxic, edible mixture containing glucosylsorbitol as a major component thereof.

8 Claims, No Drawings

PROCESS FOR THE MANUFACTURE OF GLUCOSYLSORBITOL

This is a continuation of application Ser. No. 111,272, filed Jan. 11, 1980, now abandoned.

BACKGROUND OF THE INVENTION

A condensation product of glucose and sorbitol is recognized as a suitable bulking agent suitable for use in an admixture with formulated foods, such as cakes, candy bases, preserves, puddings and the like. Bulking agents may be used alone, but often are employed with low-calorie, high-intensity, artificial sweetener products, to render the bulking agent effective and generally as sweet as sucrose.

U.S. Pat. No. 4,024,290 discloses the preparation of bulking agents by the reaction of glucose and sorbitol in the presence of an acidic ion-exchange resin, such as a sulfonated styrene-divinylbenzene resin. After separation of the inedible ion-exchange resin, the major product produced is glucosylsorbitol. The use of the ion-exchange resin requires purification procedures, such as neutralization and separation steps, prior to the production of the bulking agent. Typically, the use of strong acid, inorganic or monocarboxylic acid results in an undesirable inedible reaction product.

U.S. Pat. No. 3,766,165 relates to the preparation of polymerized polysaccharides in an anhydrous melt polymerization process employing edible acids as catalysts and cross-linking agents. The polymerized glucose-polymers with sorbital terminating groups produced are characterized by high molecular weights: for example, an average molecular weight of 6,000 to 36,000.

SUMMARY OF THE INVENTION

Our invention relates to a process for the preparation of the condensation product of glucose and sorbitol and to the product so prepared and the use of the condensation product as a food-bulking agent.

It has been discovered that glucose and sorbitol, when reacted in stoichiometric equimolar amounts with heating preferably under vacuum to remove water and in the presence of edible nontoxic, nonvolatile di or tri carboxylic acid or acid anhydrides as acid catalysts, the primary reaction product is glucosylsorbitol. This process and reaction are unusual, since it would be expected that such reaction would provide a high-molecular-weight glucose-based polymer.

The reaction product resembles sucrose in both texture and bulk. The product is more hygroscopic than sugar and is tasteless. When used with other high-intensity sweeteners, it may be incorporated in low-calorie food, imparting texture, bulk and appearance of regular food. Many materials have been proposed for use in dietetic food for this purpose, but none of these materials satisfy all of the requirements simultaneously.

Our process provides for the direct preparation of the dimer product as the major product and avoids the difficulties associated with purification steps to remove inedible acid catalysts.

The process is simply carried out under varying reaction times and temperature conditions and typically at a temperature of from about 140° C. to 180° C.; for example, 150° C. to 170° C., and in reaction times of from 30 minutes to 3 hours; for example, 30 minutes to 1½ hours. Water may be removed by carrying out the reaction under vacuum, preferably less than 20 inches of mercury.

The reaction is as follows:

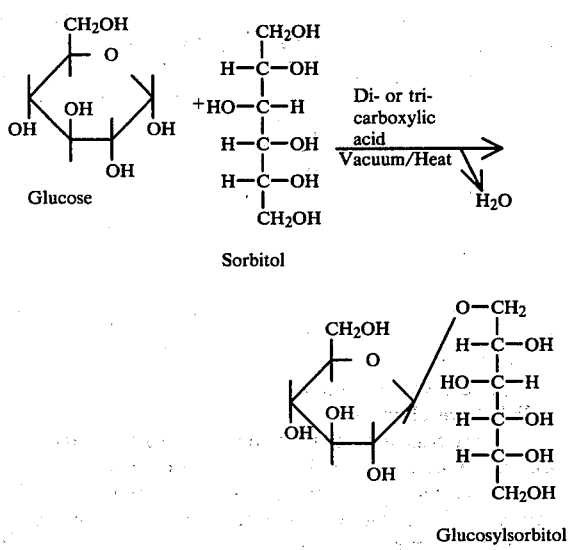

The reaction product produced is composed mainly of the dimer glucosylsorbitol, and minor amounts of the decomposition products of glucose.

The acid catalyst employed may be a nonvolatile, edible, nontoxic di or tricarboxylic acid or acid anhydride. Typical acid catalysts include, but are not limited to: citric acid, lactic acid, fumaric acid, tannic acid, tartaric acid, or adipic acid and succinic acid anhydride may be used. The amount of the acid catalyst may vary, but typically ranges from about 0.05% to 5.0% by weight of the glucose-sorbitol mixture: for example, 0.2% to 2.0%.

DESCRIPTION OF THE EMBODIMENTS

Equimolar quantities of sorbitol and glucose were weighed. Sorbitol was transferred in the reaction kettle and heated until it melted down to flowable liquid. 1% of total weight (glucose and sorbitol) of di or tricarboxylic acid was added to sorbitol. The contents of the reaction kettle were agitated for a few minutes. Glucose was then transferred to the kettle and the temperature was raised to 270° F. At this point, vacuum was applied. As the temperature reached 300° F., the reaction was stopped.

The above invention would be understood more fully in light of the following examples:

EXAMPLE 1

An intimate mixture of equimolar quantities of sorbitol, glucose (1 lb:15.8 oz.) and 1% of citric acid was placed in a vacuum kettle. It was heated to 160° C. and vacuum (30" of Hg) maintained for 1 hour. The product obtained was of light yellow color. Upon cooling, it set like a glass and was hygroscopic.

EXAMPLE 2

A change of equimolar quantities of sorbitol and glucose was placed in a vacuum kettle. The mixture was heated to 160° C. and 1% (weight of the mixture) of tartaric acid was added to it. Temperature and vacuum (30") were maintained for 1 hour. The reaction product was similar to that of Example 1.

EXAMPLE 3

A preblend of equimolar quantities of sorbitol and gluclose was placed in a vacuum kettle. 1% of fumaric acid was added to the mixture and the contents were heated to 160° C. Temperature and vacuum (30″) were maintained for 1 hour. The reaction product was of light yellow color and had more unreacted sorbitol and glucose as compared to Examples 1 and 2.

EXAMPLE 4

An intimate mixture of 1 lb. of sorbitol and 15.8 oz. of glucose, along with 0.32 oz. of succinic anhydride, was placed in a flask and melted rapidly at a temperature of 160° C. The rapid heating is required in order to minimize the loss of anhydride by sublimation. The reaction mixture was held at 160° C. and vacuum (30″) for 1 hour. A light yellow product was obtained, which has completely water-soluble.

What we claim is:

1. A process of preparing glucosylsorbitol suitable for direct use as a food-bulking agent, which process consists essentially of heating equimolar quantities of a mixture of glucose and sorbitol under vacuum in the presence of an effective amount of a nontoxic, edible, di or tri carboxylic organic acid or acid anhydride as an acid catalyst, to provide, without further purification, a nontoxic, edible, solid, light-color mixture consisting essentially of the dimer glucosylsorbitol as a major component thereof.

2. The process of claim 1 wherein the acid catalyst is present in an amount of from about 0.05% to 5.0% by weight of the glucose and sorbitol.

3. The process of claim 1 wherein the mixture is heated to a temperature of about 140° C. to 200° C. and under a vacuum greater than about 20 inches of mercury.

4. The process of claim 1 wherein the acid catalyst is selected from the group consisting of citric acid, tartaric acid, fumaric acid, lactic acid, tannic acid, succinic acid anhydride and adipic acid anhydride and combinations thereof.

5. A process of preparing glucosylsorbitol suitable for direct use as a food-bulking agent, which process consists essentially of heating equimolar quantities of a mixture of glucose and sorbitol heated to a temperature of about 140° C. to 200° C., and under a vacuum greater than about 20 inches of mercury in the presence of a nontoxic, edible, di or tri $C_2$–$C_6$ organic carboxylic acid or acid anhydride as an acid catalyst present in an amount of from about 0.05% to 5.0% by weight of the glucose and sorbitol, the acid catalyst selected from the group consisting of citric acid, tartaric acid, fumaric acid, lactic acid, tannic acid, succinic acid anhydride and adipic acid anhydride and combinations thereof, to provide a light-yellow color, nontoxic, edible, solid, hydroscopic mixture consisting essentially of the dimer glucosylsorbitol as a major component thereof.

6. The process of claim 1 wherein the acid catalyst comprises a $C_2$–$C_6$ di or tri carboxylic organic acid or acid anhydride.

7. The process of claim 5 wherein the acid catalyst is present in an amount of from about 0.2% to 2.0% by weight.

8. The process of claim 5 wherein the reaction is carried out at a temperature of from about 140° C. to 180° C. and in a reaction time of from about 30 minutes to 3 hours.

* * * * *